United States Patent [19]

Wu

[11] 4,069,016
[45] Jan. 17, 1978

[54] ASSAY FOR BILIRUBIN
[75] Inventor: Tai-Wing Wu, Rochester, N.Y.
[73] Assignee: Eastman Kodak Company, Rochester, N.Y.
[21] Appl. No.: 759,530
[22] Filed: Jan. 14, 1977
[51] Int. Cl.² .................... G01N 31/22; G01N 33/16
[52] U.S. Cl. .............................. 23/230 B; 23/253 TP
[58] Field of Search ...................... 23/230 B, 253 TP

[56] References Cited
PUBLICATIONS

Kragh-Hansen et al., Biochim. et Biophys. Acta. 365, 360–371 (1974).
Lee et al., The Journal of Pediatrics, 86, No. 2, 280–285, (1975).
Hertz, H., Scand. J. Clin. Lab. Invest. 35, 545, (1975).

*Primary Examiner*—Robert M. Reese
*Attorney, Agent, or Firm*—Ronald P. Hilst

[57] ABSTRACT

A method for the determination of bilirubin in liquid samples, particularly biological liquid samples. An assay method, as well as an analytical element, is disclosed. In accord with the assay method there are contacted together a liquid sample containing bilirubin as analyte and an interactive composition containing a bilirubin-active complex, the complex comprising a diffusible, bilirubin-displaceable, detectable ligand bound to a carrier which can also bind bilirubin. As a result of a competitive binding-displacement interaction between bilirubin and the complex, bilirubin binds to the carrier and displaces detectable ligand which can be selectively detected and used to determine the presence or amount of bilirubin. Appropriate carriers and detectable ligands can be chosen on the basis of their first order binding constants.

33 Claims, 4 Drawing Figures

ASSAY FOR BILIRUBIN

CROSS-REFERENCE TO RELATED APPLICATION

Cross-reference is made to Figueras U.S. Ser. No. 759,527, filed concurrently herewith and entitled "Element for Analysis of Liquids." Certain of the multilayer analytical elements described herein represent specific embodiments of the invention described in the aforementioned Figueras application. The invention described in the cross-referenced Figueras application was made prior to the invention described herein.

FIELD OF THE INVENTION

The present invention relates to an assay for the determination of bilirubin in various liquid samples such as biological liquids including body fluids such as blood serum, urine and the like. The assay of the invention is direct and highly sensitive and may be employed using either "wet chemistry", i.e., analytical chemical techniques sometimes referred to as solution assay techniques wherein chemical reagents are dissolved or suspended in a liquid vehicle, or "dry chemistry," i.e., analytical chemical techniques wherein chemical reagents are incorporated in various substantially "dry-to-the-touch" elements such as monolayer test strips, multilayer analytical test elements, and the like.

BACKGROUND OF THE INVENTION

Bilirubin is a degradation product of hemoglobin. It has been estimated that each day approximately 6 to 7 grams of hemoglobin is released from damaged or aged red blood cells. From this pool of hemoglobin that is rapidly destroyed within the liver, spleen, and bone marrow, approximately 200–230 milligrams of bilirubin and its derivatives are formed each day in the normal human adult. Subsequently, as a part of normal human metabolic processes the major portion of this daily bilirubin production is excreted, degraded into other derivatives, etc.

In some cases, however, an excessive amount of bilirubin occurs within the human body through overproduction of bilirubin as in the case of excessive hemolysis or by retention of bilirubin due, for example, to a liver failure. Invariably, the result of an excessive amount of bilirubin within the human body is jaundice. This widely encompassing pathological condition is characterized by markedly elevated serum bilirubin levels, for example, 10 milligrams of bilirubin per deciliter of serum or higher compared to the normal adult range of 0.1 to about 1 milligram of bilirubin per deciliter of serum, and almost always there is also present a brownish-yellow pigmentation of the skin, sclera, or mucous membranes. In addition, there is increasing evidence suggesting that excess amounts of bilirubin in the blood can lead to an undesirable increase in bilirubin concentration within body cells and interfere with various cellular processes. For example, bilirubin has been widely implicated as a potent inhibitor of many enzymatic reactions that generate energy vital to the cell. Given this background, the clinical diagnostic significance of bilirubin, in tests for liver and other related organ functions, is self-evident.

The literature on bilirubin assay methodology is quite voluminous. Good reviews outlining many of the diverse bilirubin assay techniques can be found by reference to the test entitled *Clinical Chemistry-Principles and Technics*, edited by R. J. Henry, D. C. Cannon, and J. W. Winkelman, Harper and Row Publishers, 2nd Edition, pages 1042–1079 (1974). A further review of bilirubin assay techniques appears in *Fundamentals of Clinical Chemistry*, edited by N. W. Tietz, and published by W. B. Saunders Co., pages 743–762 (1970), Perhaps the most widely used analytical procedure for bilirubin assay work has been the so-called diazo method. The diazo method employs a coupling reaction of bilirubin with a diazonium salt, such as diazosulfanilic acid, to form a pigment having an extinction coefficient higher than bilirubin by itself (which has a yellow coloration). Typically, the diazo reaction procedure for bilirubin assay includes two kinetic phases: First, a so-called "direct reaction," in which color forms quite rapidly and then an "indirect reaction," in which color develops only after the addition of methanol. As outlined in the above-noted literature reviews, particularly that of Winkelman et. al., some confusion exists in the art with respect to what these two kinetic phases actually indicate. Some people consider the direct reaction a measure of unbound or free bilirubin while the indirect reaction is considered a measure of albumin-bound bilirubin. Others have thought the direct reaction measures conjugated bilirubin while the indirect method measures the unconjugated form of bilirubin.

In addition to the above-noted confusion existing with respect to the diazo method for bilirubin assay, Winkelman et al., in their critical review of the diazo method have concluded that in view of the many variants of the diazo procedure and the complexity of the diazo reaction itself, the analytical results obtained are often different. In addition, the diazo assay method, because of its requirement of using several different reagents which must be mixed shortly before the assay determination, generally requires a fairly long period of time and can be inaccurate because of other components in human serum and other biological fluids which will also respond to diazotization.

In addition to the above-noted diazo assay method and related variants thereof for determination of bilirubin, a number of other bilirubin assay techniques have been suggested or employed at one time or another. Among others, there are various direct spectrophotometric assay techniques for bilirubin which take advantage of the molar absorbtivity inherent in bilirubin. That is, bilirubin is a yellow pigment having a molar absorbtivity of about $5 \times 10^4$ as measured at 435 nanometers. However, although the molar absorbtivity of bilirubin is high enough to be useful in various direct spectrophotometric solution assay techniques, it is not sufficiently high to produce a quantitative assay for bilirubin using "dry chemistry" analytical test elements. Thus, present-day direct spectrophotometric assay techniques for bilirubin are generally limited to solution assay techniques, particularly if accurate, quantitative results are desired. However, as noted in the above-referenced articles reviewing various bilirubin assay techniques (see the Winkelman et al, article noted above), direct spectrophotometric assay determinations for bilirubin suffer from spectral interferences due to the presence of hemoglobin which exhibits absorption peaks at 414, 540, and 576 nanometers. In addition, other materials present in bilirubin-containing biological fluids such as human serum can also cause spectral interferences using such direct spectrophotometric assay methods. For example, carotenoids can interfere with bilirubin assays because beta-carotene, one of the principal carotenoid components, exhibits an absorption peak at about 450 nm which is in a region of the spectrum close to the absorption peak of bilirubin.

In addition to the above-noted spectral interferants for bilirubin using a direct spectrophotometric assay technique, it has been found that such techniques can also suffer interference due to the presence of other protein materials in human serum, such as albumin, to which bilirubin can bind and which as a result of such binding can cause a shift in the absorption intensity and absorption peak of bilirubin. As a result of the above-noted problems, among others, the art has had to rely substantially on the aforementioned diazo assay method for bilirubin determination or upon various modifications of the above-described direct spectrophotometric determination for bilirubin. For example, in U.S. Pat. No. 3,569,721 there is illustrated a direct spectrophotometric technique for determination of bilirubin wherein the spectral interference of hemoglobin is allegedly eliminated by, in essence, measuring the fluid sample to be tested at a wavelength for bilirubin maximum absorption and at a second wavelength for which hemoglobin, alone, is known to exhibit an absorption peak. One must then adjust the absorption peak for bilirubin concentration by an amount equivalent to the amount of hemoglobin determined to be present in the liquid sample.

Still another technique which has been used for the assay of bilirubin relates to the use of a reagent composition for bilirubin containing an organic acid or its salt such as trichloroacetic acid or an organic sulfonic acid, together with a ferric ion. In this method, bilirubin is oxidized by the organic acid or its salt in the presence of the ferric ion to a reaction product such as biliverdin and/or cholecyanin, which reaction product exhibits a characteristic blue or blue-green color and intensity which is related to the amount of bilirubin originally present. Such bilirubin assay techniques are described for example in U.S. Pat. No. 3,348,920 issued Oct. 24, 1967; U.S. Pat. No. 3,607,093 issued Sept. 21, 1971; and Belgium Patent 816,927 filed October 16, 1974. However, this method also suffers from many of the drawbacks noted above with respect to the diazo assay method and the direct spectrophotometric assay method. For example, the use of this assay method employing an organic acid or acid salt together with a ferric ion generally requires a substantial amount of time involving up to about 10 minutes for the reaction between the acid and bilirubin to go to completion and then an additional amount of time required to separate the final product from the original reaction media so that it may be analyzed spectrophotometrically. In addition, this test also is subject to various spectral interferants which exhibit absorption maxima in the blue region of the spectrum such as hemoglobin, various carotenoids, and the like.

In addition to the foregoing clinical analytical techniques which have been developed for bilirubin assay work, it has been reported in the technical literature that various materials, such as bilirubin, which have a high binding affinity for proteins, such as human serum albumin, can competitively displace a colorant, such as phenol red, which is bound to albumin but which has a relatively low binding affinity for albumin. For example, bilirubin has a first order binding constant $K_A(M^{-1})$ to human serum albumin of greater than $10^8$ whereas phenol red has a similar first order binding constant $K_A(M^{-1})$ to human serum albumin of about $10^4$. (See V. Kragh-Hansen et al., "Relation Between Binding of Phenolsulfothalein Dyes and Other Ligands With A High Affinity For Human Serum Albumin," *Biochemica et Biophysica Acta*, Volume 365 (1974) p. 360–371 at page 366 and 367.) Other technical journal articles have described fluorometric or spectrometric determinations relating to the study of the bilirubin binding capacity of albumin based on the interaction of albumin with bilirubin and dyestuffs such as the fluorescent dye Vasoflavine and colored dyestuffs such as bromophenol blue. See Betheil, *Analytical Chemistry*, Vol. 4, page 560 (1960); Lee et. al., *The Journal of Pediatrics*, Vol. 86, No. 2, page 280 (1975); and Hertz, *Scand. J. Clin. Lab. Invest*, Vol. 35, page 545 (1975).

However, to the knowledge of applicant, the above-cited technical journal articles have not applied the various techniques described therein or variations thereof to develop a clinical assay for total bilirubin content of a particular biological liquid sample.

In addition, to applicant's knowledge, the art has devised no multilayer integral analytical element such as that described in Pryzbylowicz and Millikan, U.S. Pat. No. 3,992,158, issued Nov. 16, 1976 and in Clement, U.S. Ser. No. 691,265, filed June 25, 1976, for bilirubin assay which employs as a bilirubin-active reagent a competitive binding-displacement system.

SUMMARY OF THE INVENTION

In accord with the present invention there are provided a method and element for the assay of bilirubin which employ a competitive binding-displacement interaction between bilirubin and an interactive composition comprising a bilirubin-active complex. The bilirubin-active complex comprises a diffusible, bilirubin-displaceable, detectable ligand bound to a carrier which can also bind bilirubin. The carrier or binder used in these complexes exhibits a first order binding constant to bilirubin in excess of $10^7$ and a first order binding constant to the detectable ligand of the complex which is in excess of $10^5$ but less than the aforementioned binding constant to bilirubin. The method of the invention comprises (i) contacting together the bilirubin-active complex and a liquid sample to be tested for bilirubin in a reagent zone to effect displacement and release of the detectable ligand from the complex in an amount indicative of the presence or concentration of bilirubin in the test sample and (ii) selectively detecting the detectable ligand. The phrase "selective detection of detectable ligand" (as well as similar phrases) is used herein to refer to detection of the detectable ligand released from the reagent zone or the detection of unreleased ligand which remains in the reagent zone subsequent to interaction with a liquid sample being tested for the presence or concentration of bilirubin.

The method of the present invention is useful for analysis of bilirubin in biological liquid such as blood, blood serum, urine, etc., particularly blood serum, because it can minimize the effect of many common bilirubin interferents such as hemoglobin, carotenoids, biliverdin, and others. Of course, when used to analyze the bilirubin content of such biological liquids, it may still be desirable to remove and dissociate (from bilirubin) various higher molecular weight protein interferents to which bilirubin can bind, for example, albumin, so that one can obtain a quantitative analysis for total bilirubin contained in the test liquid. For this reason, in accord with one embodiment of the invention, the test liquid can be subjected to a preliminary treatment for separation or removal of such bilirubin interferents. Such preliminary treatment can comprise conventional techniques adapted for the removal of high molecular weight protein interferents for bilirubin, such as protein precipitation, sample dilution, and the like.

Alternatively, in accord with an especially preferred embodiment, the bilirubin assay described above is carried out by use of an analytical element of the invention for the detection of bilirubin in a liquid which employs a substantially "dry chemistry." Such an element comprises a reagent zone, for example, a layer comprising the above-defined bilirubin-active complex, and, optionally a spreading zone or layer which can distribute or meter the liquid test sample to the reagent zone. If desired, a surfactant can be incorporated into the spreading zone in an amount effective to normalize transport of bilirubin through this zone, even in the presence of widely varying amounts of high molecular weight protein interferents for bilirubin such as albumin and the like. If the particular liquid sample to be analyzed is first subjected to an independent preliminary treatment step for removal of substantially all protein interferents for bilirubin (e.g., protein precipitation or sample dilution), one can design an element for assay of bilirubin in accord with the present invention based solely upon the use of an element containing the above-defined reagent zone.

In accord with a further aspect of the invention, the reagent zone of the above-described analytical elements for the assay of bilirubin are preferably impermeable to higher molecular weight protein interferents for bilirubin, e.g., proteins having a molecular weight of about 60,000 (dalton units) or higher, to further alleviate interference from such materials.

In accord with a further embodiment, the elements of the invention are integral elements wherein the spreading zone, if present, and reagent zone are superposed layers carried on a suitable support, such as a "radiation-transmissive" support. As used herein, the term "radiation-transmissive" describes zones, supports, or layers of an analytical element that permit effective passage of electromagnetic radiation used to detect an analytical result produced in the element. Such transmissiveness includes transmission of electromagnetic radiation of a wavelength or wavelengths within the region between about 200 nm. and 900 nm., and also of detectable radiation as is produced by radioactivity. In accord with this embodiment of the invention, a separate registration layer may be incorporated between said reagent layer and said support, if desired, to receive the released, diffusible detectable ligand which is displaced from the bilirubin-active complex in the reagent layer of the element. The elements of this invention can also include a radiation-blocking layer, which is usually interposed between the reagent layer and the registration layer. The radiation-blocking layer is a layer that contains one or more opacifying agents and inhibits passage in or through such layer of electromagnetic radiation, such as at the wavelength or wavelengths used for excitation and/or detection of the detectable ligand within the registration layer.

In accord with the invention, the various individual layers or zones of the analytical elements described herein are, at least under conditions of use, in fluid contact with one another. Such fluid contact has reference to the ability of a liquid to pass between superposed or abutting layers or zones of an analytical element. Stated in another manner, fluid contact refers to the ability of components of a liquid to pass between the layers or zones in fluid contact. Although layers or zones in fluid contact can be contiguous, they may also be separated by intervening layers or zones. However, layers or zones in the element that physically intervene layers or zones in mutual fluid contact will also be in fluid contact therewith and will not prevent the passage of fluid between such layers or zones.

Fluid contact between layers or zones can be achieved by preparing elements having layers or zones that are initially contiguous or effectively so for purposes of fluid passage. Alternatively, it may be appropriate to prepare elements that have layers or zones initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has initially non-contiguous layers or zones, it may be necessary to apply compressive force or otherwise provide means to bring layers or zones of the element into fluid contact at the time of its use to provide an analytical result.

As used in the specification and claims herein, the term "diffusible" denotes the capability of a material to move effectively within an analytical element by diffusion when that material is carried in liquid present in the element, such as the solvent or dispersion medium of a liquid sample applied to the element. Similarly, the term "permeable" denotes the ability of a substance, layer, or zone to be penetrated effectively by a material carried, i.e., distributed in as by dissolution or dispersion, in a liquid.

In operation, an exemplary analytical element of this invention can receive a liquid sample which, if bilirubin positive, interacts with the bilirubin-active complex within the reagent layer to release a diffusible, preferably radiometrically detectable ligand that diffuses from the reagent layer into the registration layer. Selective detection of the detectable ligand can be accomplished by composing the analytical element such that the unreleased detectable ligand is selectively detected in the reagent layer without interference from the released ligand in the registration layer or vice versa. This can be done by suitable structural arrangement of the various layers of the analytical element or by appropriate selection of detectable ligand materials, both of these techniques being illustrated hereinafter. If necessary or desirable, a radiation-blocking layer can be provided in the element between the reagent layer and the registration layer, for example to screen out red blood cells, if analyzing whole blood, or to isolate other materials from being observed during detection of an analytical result in the registration layer. If a spreading layer is included in an element, an applied sample will usually pass through this layer prior to entering the reagent layer, and bilirubin analyte will be distributed within the spreading layer to provide a uniform apparent concentration of such material at the surface of the spreading layer facing the reagent layer. It is possible to obtain such uniform apparent concentration over a wide range of sample volumes applied to the element. Due to fluid contact between the spreading layer and the reagent layer and also to the preferred uniform permeability of the reagent layer to bilirubin spread within the spreading layer, uniformly metered constituents are provided from the spreading layer to the reagent layer and can penetrate the reagent layer essentially without the occurrence therein, at any instant in time, of significant variations in the apparent concentration of bilirubin. Due to the presence of the bilirubin-active complex in the reagent layer, and a uniform apparent concentration of bilirubin provided from the spreading layer to the reagent layer, a uniform quantitative detectable change can be produced in the element. Such a change, which is due to the release of a preformed ligand, detectable, for example, by an increase or decrease in coloration of fluorescence, can be detected quantitatively by radiometric techniques and, if desired, by automatic radiometric sensing devices such as photometric or fluorimetric devices.

Preferably, the bilirubin assay method of the present invention is carried out by employing analytical elements, as described above, which employ "dry chemistry." However, it will be appreciated that the method of the present invention can also be conveniently carried out using various "wet chemistry" or solution assay techniques. In such case, the bilirubin-active complex incorporated in a suitable liquid medium is contacted with a liquid sample containing bilirubin. When using a "wet chemistry" or solution assay, it is preferred to subject the bilirubin-containing liquid analyte to a preliminary treatment step for eliminating high molecular weight protein interferents for bilirubin. This can be conveniently carried out using any of the above-noted separation techniques.

BRIEF DESCRIPTION OF THE DRAWING

In the accompanying drawings, each of FIG. 1, FIG. 2.

DESCRIPTION OF PREFERRED EMBODIMENTS

Figure 1:
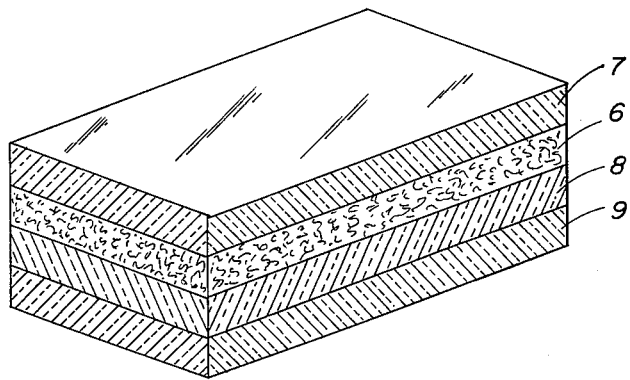

As set forth hereinabove, an essential feature of the present invention is the use of an interactive composition comprising a bilirubin-active complex of certain diffusible, bilirubin-displaceable detectable ligand(s) bound to an appropriate carrier. When such a composition comes into fluid contact with a bilirubin-containing liquid, bilirubin competes for and displaces from the carrier an amount of the detectable ligand which is bound to the carrier at binding sites common to both bilirubin and the ligand. In accord with certain preferred embodiments of the present invention, it has been found that by selection of appropriate ligands and carrier to form a bilirubin-active complex, the present invention can provide an accurate, quantitative method for determination of bilirubin in blood serum due to the direct, substantially stoichiometric displacement of the detectable ligand by bilirubin.

By selection of appropriate detectable ligands and carriers for use in preparing the bilirubin-active complex which comprises the interactive composition used in the invention, one is provided with a bilirubin assay technique which is not only accurate but which, in accord with certain preferred embodiments of the invention, is rapid, sensitive, and can be used to determine widely varying amounts of bilirubin present in a liquid sample, e.g. blood serum, without the use of sample dilution. Moreover, when using the preferred integral analytical elements described herein for carrying out the method of the invention, one can obtain a quantitative determination for bilirubin in blood serum which, unexpectedly, is substantially free from interference caused by high molecular weight proteins present in such samples, such as albumin, etc. as well as bilirubin spectral interferents such as hemoglobin, bile pigments (which contain carotenoids), and certain drugs, all of which can have serious adverse effects on bilirubin determinations performed by various prior art techniques such as those described hereinabove.

The carrier which serves as a common carrier or binder to which the detectable ligand and bilirubin are bound can be selected from a variety of different materials including proteins such as albumin; albumin fragments such as degradation products of albumin and albumin derivatives such as crosslinked albumin molecules, e.g., carboxy methylated albumin; various serum globulins such as $\alpha$-, $\beta$-, and $\gamma$- globulin and macroglobulin; lipoproteins such as used in various commercially available biomembrane materials; and glycoproteins. In addition, various agarose materials, often referred to as polysaccharides, may also be used as carriers. For example, polyglucose materials can be employed. In addition, various polymeric mordants have also been found useful as carriers to which bilirubin binds.

In the present invention two ligands, namely bilirubin and the detectable ligand, compete for binding to either the same or topologically distinct site(s) on the same macromolecular carrier, and the presence or concentration of the stronger binding ligand, i.e., bilirubin, is determined by following changes in some physicochemical parameter of the weaker detectable ligand which is successively displaced by increasing levels of the competing bilirubin ligand. Therefore, the carrier substrate chosen is a material exhibiting a stronger binding affinity for bilirubin than for the detectable ligand. Thus, one must choose as a carrier a material to which the detectable ligand of choice exhibits a lower binding contant than does bilirubin. In addition, of course, the binder employed as the common carrier for the detectable ligand and bilirubin is a carrier having binding sites for which both the detectable ligand and bilirubin compete. To aid in expressing this interrelationship between the detectable ligand and bilirubin which compete for binding sites on a common carrier substrate, the term "bilirubin displaceable" is used in the present specification and appended claims.

Biological fluids such as blood and blood serum are known to contain a number of materials including various proteins, such as hemoglobin, albumin, etc.; lipids, such as oleates and palmitates; and hormones such as L-thyroxine, L-tryptophan, estradiol, progesterone, cortisol, aldosterone, testosterone, prostaglandin, urate, and the like; all of which exhibit varying degrees of binding affinity to many of the same sorts of macromolecular carrier materials to which bilirubin can be bound. Thus, in accord with the invention, it has been found desirable to select as the binder or carrier for the complex of the interactive composition a material to which bilirubin exhibits an especially strong binding affinity. In this regard, it has been found that useful binder materials are those to which bilirubin exhibits a binding constant in excess of $10^7$, preferably in excess of $10^8$, as measured by the method of Kragh-Hansen and Moller, *Biochim. Biophys. Acta,* Vol. 295, pp. 438–446 (1973). Preferred among such useful carrier or binder materials are the above-noted albumin materials, including various degradation products and derivatives thereof. By using these preferred carrier materials, one can effectively avoid as potential interferants most, if not all, of the above-mentioned proteins, lipids, and hormones because many such materials have binding constants to albumin materials which are much lower than $10^7$. For example, as shown in Table I many of those potential interferents have a binding constant to albumin, a preferred carrier, which is less than $10^5$.

TABLE I

Binding Constants of Selected Ligands to Human Serum Albumin

| Ligand or Blood Component | Binding Constant of primary or high affinity site(s) $K_A (M^{-1})$ | pH | Temperature (° C) |
|---|---|---|---|
| Bilirubin | $1.4 \times 10^8$ | 7.4 | 37 |
|  | $2.4 \times 10^8$ | 7.4 | 25 |
| Oleate and palmitate | $10^6$ | 7.4 | 23 |
| L-thyroxine | $10^6$ | 7.4 | 24 |
| L-tryptophan | $1.6 \times 10^4$ | 7.4 | 2 |
| Estradiol | $1 \times 10^5$ | 7.4 | 5 |
| Progesterone | $3.7 \times 10^4$ | 7.4 | 5 |
| Cortisol | $5 \times 10^3$ | 7.4 | 5 |
| Aldosterone | $<5 \times 10^3$ | 7.4 | 5 |
| Testosterone | $4.2 \times 10^4$ | 7.4 | 25 |
| Prostaglandin | $7 \times 10^4$ | 7.5 | 37 |
| Urate | $3 \times 10^2$ | 7.4 | 37 |
| Phenylbutazone | $4.3 \times 10^4$ | 7.4 | 37 |
| Sulfisoxazole | $1.9 \times 10^4$ | 7.4 | 37 |
| Sulfadiazine | $8.2 \times 10^2$ | 7.4 | 37 |
| Sulfanilamide | $<2 \times 10^1$ | 7.4 | 37 |
| Sodium salicylate | $9.2 \times 10^3$ | 7.4 | 37 |
| Acetylsalicylate | $5.3 \times 10^2$ | 7.4 | 37 |
| Sodium benzoate | $1.7 \times 10^3$ | 7.4 | 37 |
| Gentamicin sulfate | $<1 \times 10^1$ | 7.4 | 37 |
| Polymyzin B sulfate | $<1 \times 10^2$ | 7.4 | 37 |
| Dipheylhydantoin | $6 \times 10^3$ | — | 37 |

The diffusible bilirubin-displaceable, detectable ligand employed as a competing ligand for the interactive compositions described herein can be selected from a wide variety of such materials. As indicated above, useful such ligands are detectable moieties which have a binding affinity for the carrier of the interactive composition which is not so strong as that exhibited by bilirubin. Typically, therefore these ligands have a binding constant to the carrier which is less than about $10^7$. In addition, useful such ligands should have a minimum binding constant to the carrier which is greater than about $10^5$ so that various proteins, lipids, hormones, etc. such as those indicated in Table I do not interfere with the bilirubin assay of the invention. And, of course, as indicated, useful such ligands must be "bilirubin-displaceable," i.e., they must possess one or more binding sites on the carrier which are also common to bilirubin (it is these common binding sites to which the above-noted binding constant criteria relates).

Typically, in accord with a preferred embodiment of the invention, the detectable ligand represents a chemical moiety or precursor thereof whose presence can be determined radiometrically. Radiometric analyses can include many different detection means, including sensing devices which detect radio emissions from such detectable moieties, for example, detectable ligands which phosphoresce, fluoresce, or which exhibit radioactive emissions. In addition, radiometric sensing means include colorimetric sensing devices which detect the presence of the desired ligands due to a characteristic absorption spectra or extinction coefficient. It is especially preferred to use colorimetrically detectable moieties which exhibit such a spectral shift to a wavelength greater than approximately 460 nanometers because free bilirubin exhibits an absorption spectra at approximately 435 nanometers and "bound" bilirubin (i.e., bilirubin bound to common protein carriers such as albumin) exhibits an absorption peak at about 460 nanometers. Moreover, many known bilirubin interferents, such as various high molecular protein interferents and other biological interferents, are known to exhibit absorption in regions of the spectrum below 460 nanometers. For example, various bile pigments contain $\beta$-carotene which is a common bilirubin assay interferent and exhibits absorption in a region of the spectrum at about 450 nanometers. Also, hemoglobin exhibits a strong absorption peak at about 414 nm.

Among detectable moieties which have been found particularly useful in the present invention are ligands which exhibit a high degree of fluorescence in their bound state, i.e., when bound to the carrier in the bilirubin-active complex, and which exhibit little or no fluorescence in their free state upon displacement and release from the bilirubin-active complex. Such ligands can be readily detected by looking for and following the decrease in fluorescence emission of the bilirubin-active complex caused by the release of the free form of the ligand (which, as noted above, exhibits little or no fluorescence.) Accordingly, it will be appreciated that the term "detectable ligand" or "detectable moiety" as used herein refers to materials which are detectable in either their free state or their bound state, the essential requirement of such "detectable" materials being that there exist a detectable difference between their "bound state" in the bilirubin-active complex and their released state (or as explained immediately hereinafter the reaction product produced from the material in its released state and another reagent).

It will be appreciated that the terms "detectable moiety" and "detectable ligand" as used in the present specification and appended claims can also include those materials which although not detectable in their released state can be rendered detectable upon reaction of the "detectable" ligand in its released state and another suitable reagent. For example, a suitable detectable ligand can comprise a photographically useful material such as a dye precursor, for instance, a coupler, which upon release can thereafter form a detectable colorant such as a pigment or dye by undergoing a color forming coupling reaction. Such materials are well known, for example, in conventional silver halide photography and extended discussion thereof in the present application is deemed unnecessary. If desired, additional information concerning such materials may be found by reference to paragraph XXII appearing in the article entitled "Photographic Elements and Processes," appearing in *Research Disclosure*, Vol. 92, publication 9232, page 110, dated December, 1971. *Research Disclosure* is a publication of Industrial Opportunities Ltd. having the address Homewell, Havant, Hampshire, P09 IEF, United Kingdom.

As will be appreciated from the above discussion, a further feature of the "detectable" ligand useful in the bilirubin-active complexes employed in the present invention is that this ligand is not chemically generated as the result of a chemical reaction. Rather, it is performed and is physically or chemically released, intact, from the complex to which it is bound whereupon its presence is directly detectable (or can be so rendered) without interfering with the displacement or release of this ligand from the bilirubin-active complex.

As specific examples of detectable ligands which have been found useful in the present invention, mention may be made of the following partial listing of representative materials: Suitable detectable ligands which may be detected by changes in fluorescence between the ligand in its bound state and in its free state include materials such as an 8-anilino-1-naphthalenesulfonate salt (hereinafter referred to as ANS), a 6-p-toluidino-2-naphthalene-sulfonate salt (TNS), a 5-dimethylamino-1-naphthalene sulfonate salt (DANS), as well as various thioflavine dyestuffs such as thioflavine S, a sulfonated methylated benzothiazole derivative. Other useful fluorescent probes include acridine orange, a 5-[N-(2-iodoacetylaminoethyl)amino]-1-naphthalene sulfonate salt, m-trimethylammoniumphenylanthranilate, and the sulfonyl chloride salts of TNS and DANS. Many of these ligands detectable by fluorescence, such as ANS, TNS, DANS, etc., represent known fluorescent probes and are commercially available, for example, from Eastman Organic Chemicals. A partial listing of representative colorimetrically detectable ligands useful in the present invention include dyestuffs such as bromophenol blue, chlorophenol red, and the like. Preferably, these colorimetrically detectable ligand materials exhibit a molar extinction coefficient of 75,000 or greater so that they can readily be detected by conventional colorimetric detection devices.

The amount of the above-described bilirubin-active complex required in the bilirubin assay of the invention can vary. In many cases, because the displacement and release of detectable ligand can bear a stoichiometric relation to the amount of bilirubin which displaces such ligand, the amount of such bilirubin-active complex can be readily determined based on this stoichiometric relation, depending, in any given case, upon the particular range of bilirubin content, i.e., the "dynamic range," over which a specific bilirubin assay is designed to be useful. In general, one mole of bilirubin displaces at least one mole of ligand from the bilirubin-active complex contained in a given test element so that there should be sufficient complex to provide at least a molar equivalent amount of ligand equal to the maximum number of moles of bilirubin for which that element is capable of analyzing. In accord with various preferred embodiments of the invention, one mole of bilirubin is capable of displacing 2 or more moles of detectable ligand from the bilirubin-active complex. Generally, it has been found that useful amounts of carrier material in the bilirubin-active complex in accordance with the invention are within the range of from about 1 to about 10 or more moles of carrier per mole of bilirubin analyte. As will be appreciated, the amount of individual detectable ligand and carrier material used in a given complex will depend upon the specific carrier material and detectable ligand used to form such complex. For example, in a preferred embodiment of the invention using ANS, a fluorescent probe, as the detectable ligand and albumin as the carrier, it has been found that the ANS-albumin complex contains from 2 to about 7 moles of ANS for each one mole of albumin. In general, it has been found that one can extend the "dynamic range" of a test element of the invention most easily by increasing the absolute amount of both detectable ligand and carrier used in a specific bilirubin-active complex, rather than by trying to hold either the absolute amount of detectable ligand or carrier constant and substantially changing the molar amount of the other component of the complex, i.e., the carrier or detectable ligand, respectively.

As noted earlier herein, the method of the present invention may be carried out as a solution assay, or in accord with a preferred embodiment of the invention by use of "dry chemistry" employing, for example, an integral analytical element of the invention. When the method of the invention is carried out as a solution assay, one carries out an analysis by first preparing in a suitable "wet" reaction zone, such as a radiation-transmissive container, an appropriate interactive composition, as described above, dissolved or dispersed in a non-interfering liquid medium. Such non-interfering liquids include those liquid materials which, under conditions of use, do not substantially interfere with the displacement and release of detectable ligand. In addition, of course, the liquid medium should be chosen such that it does not interfere with the particular radiometric method employed to detect for the released ligand. Such non-interfering liquids include a variety of both aqueous and organic liquids. Typically, because of the application of the methods of the present invention to the analysis of biological fluids, it is advantageous to choose as the non-interfering liquid used in the reaction zone, an aqueous liquid such as water or various similar polar organic solvents, e.g. lower alkyl alkanols. If desired, depending upon the particular interactive composition, it may be useful to include various buffering materials in the reaction zone, in addition to the interactive composition. In general, bilirubin assays carried out by "wet chemistry" techniques in accord with the present invention have been found to yield advantageous results when carried out using a buffered aqueous liquid having a pH range of from about 6.8 to about 9.5 and at a temperature within the range of from about 15° to about 60° C, preferably from about 22° to about 50° C. Of course, depending upon the particular interactive composition selected, one can vary the aforementioned pH and temperature of the reagent zone to values above or below the aforementioned ranges providing, of course, that one does not use a pH or temperatures which causes undesired side reactions or significant degradation of the bilirubin analyte. In addition, when the method of the invention is carried out as a solution assay, it is desirable to carry out the assay in the dark or under yellow safelight conditions to avoid light induced degradation of bilirubin.

When the method of the present invention is carried out as a "wet" assay for bilirubin, it is desirable, as explained hereinabove, to first preliminarily treat the bilirubin-containing liquid test sample to dissociate the bilirubin from various materials to which it may be bound. For example, where the liquid test sample is blood serum, it is known that a large amount of the bilirubin in the serum is bound to albumin also present in the serum. Various techniques have been devised in the art to dissociate bilirubin from materials such as albumin, and such methods may be employed as a preliminary treatment step in accord with the method of the present invention so that the resultant assay provides an accurate determination of total bilirubin contained in the serum sample. Such known methods for affecting dissociation between bilirubin and various serum protein, particularly albumin, include the use of various protein precipitation techniques, sample dilution techniques; and the like. A brief review of many of these different procedures may be found for example in Winkelman, Cannon and Henry in *Clinical Chemistry-Principles and Technics,* Second Edition, 1974, pages 1042 through 1079.

Figure 2:
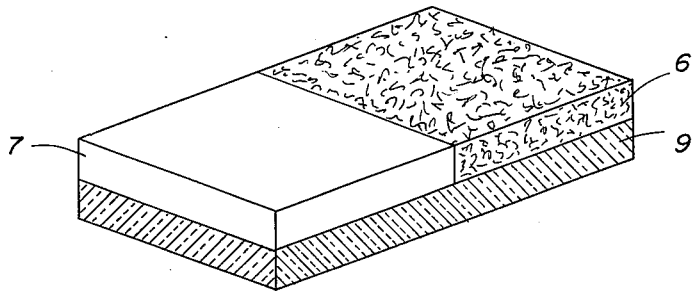

As noted hereinabove, the bilirubin assay method of the present invention is adaptable to both solution and the so-called "dry" chemical analysis techniques. As further noted, because of handling ease and other overall convenience features as well as the ability to provide quantitative analytical results, the use of the present invention in an analytical element as illustrated in FIGS. 1 and 2 for the "dry" analysis of bilirubin is especially preferred. Such an element, as illustrated in FIG. 1, comprises an initially dry reagent zone 6 containing the above-described bilirubin-active complex. Although not required, an initially dry spreading zone 7 and/or registration zone 8 can also be present in the analytical element so that a preferred analytical element of the invention typically comprises at least two distinct zones which are in fluid contact with one another under conditions of use. Preferably, the various zones are present in an element of the invention as superposed, contiguous layers. Typically, these layers are coated on a support 9, preferably a radiation transmissive support. It will be appreciated, however, that although preferred analytical elements of the invention are composed of superposed, contiguous layers, other elements may also be prepared in accord with the invention having a different structural arrangement such as the use of an element as shown in FIG. 2 having at least two adjacent abutting zones, e.g., a spreading zone 7 and a reagent zone 6, carried on a support 9, if necessary or desired. For purposes of convenience and for illustrating the best mode of the invention, the elements of the present invention will hereinafter be described in terms of their structure and characteristics as observed in a multilayer, integral analytical element wherein the different zones are present as superposed, contiguous layers carried on a radiation transmissive support.

An integral element of the invention need only include a reagent layer. However, typically a preferred element also includes a spreading layer and/or a registration layer, the latter layer, if present, preferably being radiation-transmissive. Such elements can have the layers on a support, preferably radiation-transmissive; however, if the layers demonstrate appropriate durability and integrity, a support is not needed.

In one preferred embodiment, an integral analytical element of this invention comprises a radiation-transmissive support having thereon, (1) a reagent layer that is permeable to at least bilirubin and which contains an interactive composition comprising a bilirubin-active complex as described above, (2) a radiation-blocking layer that is permeable to the detectable ligand released from the bilirubin-active complex, and (3) a radiation-transmissive registration layer that is permeable to the detectable ligand released from the bilirubin-active complex and within which the detectable ligand can be detected. Optionally, the registration layer can include a mordant for the detectable ligand. The registration layer is preferably interposed between the support and the radiation-blocking layer, with the radiation-blocking layer interposed between the registration layer and the reagent layer. Also, the reagent layer is preferably of substantially uniform permeability to bilirubin and to the diffusible, detectable ligand but is substantially impermeable to protein materials having a molecular weight substantially greater than that of bilirubin, e.g., albumin, etc. The registration layer is of uniform permeability as regards the detectable ligand. The radiation-blocking layer, although usually not considered disruptive of the apparent concentration of detectable ligand provided to the radiation-blocking layer from the reagent layer, is desirably of uniform permeability to the detectable ligand. Preferred radiation-blocking layers include an opacifying agent such as a pigment, a polymer in appropriate form, such as a blushed polymer, or both. In one aspect of this embodiment, the radiation-blocking layer and registration layer are non-fibrous.

In accordance with another preferred embodiment of the present invention, there is provided an integral analytical element with a support having thereon a registration layer, a reagent layer and, optionally, a radiation-blocking layer, all as described above with respect to the foregoing preferred embodiment. Additionally, however, there is included in elements according to this preferred embodiment a non-fibrous spreading layer, desirably isotropically porous and positioned in the element such that the reagent layer is interposed between the registration layer and the spreading layer. In one aspect of this embodiment, all layers are preferably non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading as discussed herein or with detection of the analytical result by radiometric means.

When used in association with a spreading layer, reagent layers in the elements of this invention are desirably uniformly permeable to bilirubin but substantially impermeable and nonporous to other higher molecular weight protein materials spreadable within the spreading layer. As used herein the term permeability includes permeability arising from porosity, ability to swell or any other characteristic. Reagent layers can include a matrix in which the interactive composition is distributed, i.e., dissolved or dispersed. However, where the bilirubin-active complex is itself film-forming or otherwise readily coatable as a uniform layer or zone, such an additional matrix material is not required. The choice of a matrix material is, of course, variable and dependent on the components of the bilirubin-active complex distributed therein. In any case, the matrix material should be "non-interfering" with respect to the bilirubin-active complex, i.e., the matrix material should be incapable of itself binding to and displacing the detectable ligand from the carrier material of the bilirubin-active complex. Desirable matrix materials for reagent layers are non-fibrous and can include non-interfering hydrophilic materials including acid-hydrolyzed gelatins, e.g., pigskin gelatins, or derivatives thereof having an isoelectric point of about 9.1, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Non-interfering organophilic materials such as cellulose esters and the like can also be useful. To enhance permeability of the reagent layer, if not porous, it is often useful to use a matrix material that is swellable in the solvent or dispersion medium of liquid under analysis. Also, it may be necessary to select a material that is compatible with the application of an adjacent layer, such as by coating means, during manufacture of the element. As an example, where the formation of discrete, contiguous layer is desired and the intended analysis will be of aqueous liquids, it may be appropriate to select an essentially water soluble matrix for the reagent layer and essentially organo-soluble or organo-dispersible ingredients for an adjacent layer, such as a spreading layer. In such manner, mutual solvent action is minimized and a clearly delineated layer structure can be formed. In many cases, to prevent diffusion of high molecular weight protein materials into the reagent layer (which materials may be potential bilirubin interferents), it may be desirable to have the reagent layer of lower permeability than is the spreading layer itself. This can readily be accomplished by reducing the effective pore size of the reagent layer. Relative permeability or porosity can be determined by well-known techniques.

Within the reagent layer is distributed an interactive composition, including one or more of the above-described bilirubin-active complexes. The distribution of interactive composition can be obtained by dissolving or dispersing it in a matrix material, if used. Although uniform distributions are often preferred, they may not be necessary. Interactive compositions soluble in the liquid under analysis may advantageously be immobilized in the reagent layer, particularly when the reagent layer is porous. In the practice of this invention, the detectable ligand of the interactive composition is diffusible such that it can move into the permeable registration layer. Such diffusivity can be imparted to detectable ligands not inherently diffusible by means known to those skilled in chemical synthesis, usually by the addition of chemical groups that impart the desired solubility. Where aqueous liquids are to be analyzed, solubilizing groups such as hydroxyl groups, carboxyl groups, sulfonic acid groups and the like can be useful for purposes of solubilization.

As is the case for a "wet chemistry" or solution assay using as the interactive composition a bilirubin-active complex as described herein, one can also include in a "dry chemistry" analytical element of the invention an appropriate pH buffering composition. The buffering composition can be incorporated in the reagent layer or in one or more of the other layers present in a particular analytical element of the invention in an amount effective to impart to the reagent layer, under conditions of use of the element, a pH essentially identical to that employed in a solution assay. Representative of specific buffering compositions which can be used are those buffering compositions set forth hereinafter in the Examples as well as others which can provide the desired pH, such as may be described by Good in *Biochemistry*, 5, 467 (1966).

Figure 3:
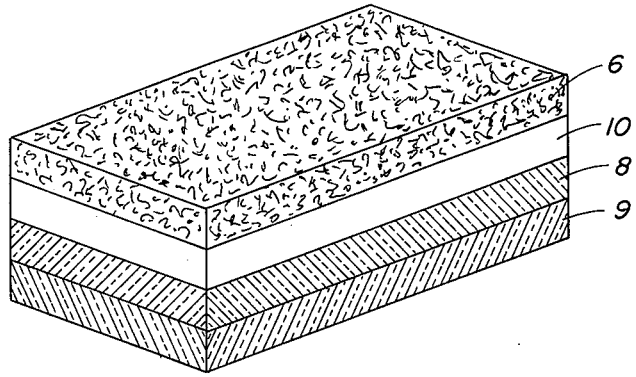
FIG. 3 is an enlarged sectional view of a preferred embodiment illustrating an analytical element of the invention.

To facilitate the detection of any change produced in an element as described herein, such as change in coloration, optical density or fluorescence, the elements of this invention can optionally include a radiation-transmissive layer to receive the detectable ligand released from the reagent layer, the relative presence or absence of which relates to detection of an analytical result. Such a layer, referred to herein as a registration layer, is free from indicating reagents, but is permeable to detectable ligands released in the element and is in fluid contact with a reagent layer, at least under conditions of use. The registration layer may be separated from reagent layer(s) by a radiation-blocking layer, such as a reflecting and/or opaque layer, to facilitate result detection by various radiometric techniques. The use of a registration layer and radiation-blocking layer are particularly desirable in cases where the detectable ligand is a colorant and is detected colorimetricaly. In such cases, as illustrated in FIG. 3, it is often desirable to include a registration layer 8 and radiation-blocking layer 10 so that the colored ligand which remains unreleased in the bilirubin-active complex of the reagent layer 6 does not interfere with the colorimetric detection of the released colored ligand. Of course, where the detectable ligand is detected fluorimetrically by detecting the change in fluorescence between the bound and released or unbound ligand, the masking of the reagent layer, although useful in certain cases, is generally not as important as in the case of a colorimetrically detectable ligand. The registration layer, which is also desirably swellable in liquid under analysis, can include hydrophilic colloids such as those useful in reagent layers and is preferably non-fibrous. When a reagent layer is fibrous, non-fibrous radiation-blocking and registration layers in association therewith improve the apparent uniformity of an analytical result produced in such a reagent layer.

Where the detectable species produced in the element is a dye or other mordantable material, the registration layer may contain a mordant, such as those described as useful image dye mordants in color photographic films and papers. Exemplary mordants are materials including vinylpyridine compounds such as poly-4-vinylpyridine, the 2-vinyl pyridine polymer metho-p-toluene sulfonate and similar compounds described in U.S. Pat. No. 2,498,430 issued Oct. 11, 1949, and cetyl trimethylammonium bromide.

In accord with a preferred embodiment of the invention, it has been found particularly useful to incorporate in the registration layer basic polymeric mordant such as described in British Patent No. 1,261,925; U.S. Pat. Nos. 3,625,694; 3,709,690; 3,773,509; 3,859,096; 3,898,088; 3,958,995 and in Campbell et al., U.S. Ser. No. 525,248 filed Nov. 19, 1974. Particularly useful such polymeric mordants are those materials having in the polymer chain monomeric units of the formula

I.

wherein A represents an organo group, such as an alkylene group, forming a portion of the polymer backbone; Q represents a chemical bond or an organo group linking M⊕ to A; M⊕ represents a quaternary ammonium or phosphonium group and X⊖ represents an anion. The preferred polymeric mordants of Formula I above have been found particularly useful in analytical elements of the invention which employ a dye as the detectable ligand released from the interactive composition contained in the reagent layer.

As mentioned previously, elements of this invention can include a radiation-blocking layer, preferably interposed between a reagent layer and the registration layer. Radiation-blocking layers are permeable to the detectable ligand released in the element and serve to inhibit passage of electromagnetic radiation, such as at the wavelength or wavelengths used for detection. Using such a layer, color or other potential interferents to result detection can be kept from the registration layer. Such layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent and layers of such blushed polymers as are useful in spreading layers (as described hereinafter) can be used also as radiation-blocking layers. It will be appreciated that if a microporous, blushed polymer layer is used as a radiation-blocking layer, such layer can also serve as a filtering layer. Such a layer is useful in the event that the registration layer is permeable to filterable substances which could impair result detection in the registration layer if allowed to enter the registration layer from the reagent layer.

In one preferred aspect, blushed polymer layers can also incorporate a reflective inorganic pigment, such as the highly reflective pigments mentioned elsewhere herein, to enhance reflectivity and/or spreading (as described hereinafter). The amount of pigment that can be included in a layer together with blushed polymer is highly variable, and amounts of from about 5 percent by weight to about 1,000 percent by weight of pigment based on the weight of blushed polymer are preferred, with a pigment concentration of from about 100 weight percent to about 600 weight percent pigment based on the blushed polymer being most preferred.

As mentioned previously, an element of this invention can optionally include a spreading layer. The spreading layer is a layer that can accept a liquid sample, whether applied directly to the spreading layer or provided to it from a layer or layers in fluid contact with the spreading layer, and within which the solvent or dispersion medium of the sample and bilirubin is distributed such that a uniform apparent concentration of bilirubin is provided at the surface of the spreading layer facing the reagent layer of the element. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The mechanism of spreading is not fully understood, but it is believed that spreading results from and is limited by a combination of forces such as hydrostatic pressure of a liquid sample, capillary action within the spreading layer, surface tension of the sample, wicking action of layers in fluid contact with the spreading layer, and the like. As will be appreciated, the extent of spreading is dependent in part on the volume of liquid to be spread. However, it should be emphasized that the uniform apparent concentration obtained with spreading is substantially independent of liquid sample volume and will occur with varying degrees of spreading. As a result, elements of this invention do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g. 1 square centimeter), there is no need to remove excess moisture from the element after application of a liquid sample. Further, because spreading occurs in the spreading layer and the spread substance is provided to the fluid contacting reagent layer and without apparent substantial lateral hydrostatic pressure, there is not the "ringing" problem often seen with prior analytical elements.

The spreading layer need only produce a uniform apparent concentration of spread substance per unit area at its surface facing a reagent layer with which the spreading layer is in fluid contact, and it is very convenient to determine whether a particular layer can be suitable for spreading purposes. Such uniformity of apparent concentration can be determined by densitometric or other analytical techniques such as described in detail in U.S. Pat. No. 3,992,158.

Useful spreading layers are desirably isotropically porous layers. Reference herein to isotropic porosity identifies the fact of porosity in all directions within the spreading layer and further description of this term can be found in U.S. Pat. No. 3,992,158.

Useful spreading layers can be prepared using a variety of components as described in U.S. Pat. No. 3,992,158. Spreading layers can be prepared by coating from solution or dispersion. As stated previously, spreading and associated layers of an element are in a superposed relationship such that a spreading layer is in fluid contact with a reagent layer. The range of materials useful for inclusion in any spreading layer will usually include predominantly materials that are resistant to, i.e. substantially insoluble in and non-swellable upon contact with water or other liquid under analysis. Swelling of about 10–14% of the layer's dry thickness may be normal. The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements.

In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers, e.g., microcrystalline cellulose.

As an alternative or in addition to such particulate materials, the spreading layer can be prepared using isotropically porous polymer compositions as also described in U.S. Pat. No. 3,992,158. It is possible to prepare such polymer compositions using techniques useful in forming blushed polymers, for example, as described in U.S. Pat. No. 3,555,129. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575.

In preparing integral analytical elements of this invention, the layers can be preformed as separate layers which can thereafter be laminated prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well-known in the preparation of light-sensitive photographic films and papers. If it is essential or desirable that adjacent layers be discrete, and maintenance of layer separation by adjustment of coating formulation specific gravity is not satisfactory, as possibly in the case of porous spreading layers, the appropriate selection of components for each layer, including solvent or dispersion medium, can minimize or eliminate interlayer component migration and solvent solvent effects, thereby promoting the formation of well-defined, discrete layers. Any interlayer adhesion problems can be overcome without harmful effect by means of surface treatments including extremely thin application of subbing materials such as are used in photographic films.

For coatable reagent layers, a coating solution or dispersion including the matrix and incorporated interactive compositions can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. Fibrous reagent layers can be formed by impregnation of a fibrous matrix, in accordance with well-known techniques.

Radiation-blocking layers and registration layers can be prepared using methods and thicknesses as used when preparing coatable reagent layers, but with constituents appropriate for the particular layer. In the case of registration layers, in addition to their permeability and radiation-transmissiveness, they are desirably substantially free from any characteristic that might appear as or contribute to mottle or other noise in the detection of an analytical result produced in an integral element of the invention. For example, any variations in color or in texture within the registration layer, as could occur if fibrous materials, e.g., some papers, are used as a permeable medium, may be disadvantageous due to non-uniform reflectance or transmittance of detecting energy. This is also true regarding layers, e.g., radiation-blocking and reagent layers, of which at least the lower surface would be observable by a detection means examining a radiation-transmissive registration layer. Further, although fibrous materials like filter and other papers are generally permeable overall, some such materials typically can exhibit widely ranging degrees of permeability and may not exhibit uniform permeability, for example, based on structural variations such as fiber dimensions and spacing. As a result, such materials are not preferred in registration layers and other layers of elements of the present invention intended for quantitative analytical work.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 200 nm and about 900 nm as well as radiation due to radioactivity. For fluorimetric detection of analytical results through the support, it is desirable for the support to transmit over a somewhat wider band than is necessary for non-fluorescence measurements, or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer, the radiation-blocking layer (if present) and the registration layer will usually be interposed in the element between the support and the spreading layer (if present), which often is the outermost layer in an element.

The components of any particular layer of an element of this invention, and the layer configuration of choice, will depend on the use for which an element is intended. As stated previously, spreading layer pore size can be chosen so that the layer can filter out undesirable sample components such as proteins having a higher molecular weight than bilirubin and that would, for example, interfere with the analytical displacement reaction or with the detection of any test result produced within the element. For analysis of whole blood, porous layers having a pore size of from 1 to about 5 microns are particularly useful in screening out blood cells, which typically have a size of from about 7 to about 30 microns. If desirable, an element can include a plurality of spreading layers, each of which may be different in its ability to spread and filter.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an aid such as a surfactant. In particular, it can be desirable to incorporate a relatively large amount of a surfactant, such as a non-ionic surfactant, in the spreading layer of the elements of the invention to normalize transport of bilirubin contained in an aqueous proteinaceous liquid sample in and through this layer of the element. Such normalization refers to obtaining within the spreading layer an equivalent penetration of the solvent medium and bilirubin contained in various applied samples of aqueous proteinaceous liquids, notwithstanding variations in protein concentration between such samples. In addition, it has been found that in the total bilirubin assay of the invention wherein bilirubin is often present in a "bound-state" such as bound to other proteins, e.g., serum albumin, the use of such non-ionic surfactants in the spreading layer to achieve normalization of bilirubin transport advantageously appears to dissociate bilirubin bound to such protein. Preferred amounts of surfactant effective to achieve normalized bilirubin transport are typically between about 1% and about 15% by weight based on the dry weight of the layer. Further details regarding this use of surfactant materials to achieve normalized analyte transport may be found by reference to Goffe et al., copending U.S. patent application Ser. No. 680,619, filed Apr. 26, 1976.

Analytical elements of the present invention can be adapted for use not only in the field of clinical chemistry, but in chemical research and in chemical process control laboratories. They are well suited for use in clinical testing of body fluids, such as blood, blood serum and urine, since in this work a large number of repetitive tests are frequently conducted and test results are often needed a very short time after the sample is taken. In analyzing blood with the analytical element of this invention, the blood cells may first be separated from the serum, by such means as centrifuging, and the serum applied to the element. However, it is not necessary to make such separation, for example, if reflective spectrophotometric analysis techniques are used to quantify or otherwise analyze for the preformed detectable ligand in the element. Whole blood can be applied directly to the element and the blood cells filtered out and excluded from the registration layer through the action of a filtering layer, which can also be a radiation-blocking layer. The presence of these cells on the element will not interfere with spectrophotometric analysis if it is carried out by reflection techniques, with light being transmitted through the support and registration layer and reflected from the radiation-blocking layer or other reflecting layer such that detecting radiation does not intercept the cells. A particularly significant advantage of the integral analytical elements described herein is their ability to be used to analyze either serum or whole blood.

As can be appreciated, a variety of different elements, depending on the analysis of choice, can be prepared in accordance with the present invention. Elements can be configured in a variety of forms, including elongated tapes of any desired width, sheets or smaller chips.

The prepared integral elements are placed in use by applying to the element a sample of liquid under analysis. Typically, an element will be formed such that an applied sample will contact a spreading layer, if present, prior to the spreading reagent layer and will first contact such spreading layer at its surface furthest removed from such reagent layer. Because analytical accuracy of the present elements is not substantially diminished by variations in the volume of applied samples, especially when a spreading layer is present in the element, sample application by hand or machine is acceptable. For reasons of convenience in detecting an analytical result, however, reasonable consistency in sample volume may be desirable.

In a typical analytical procedure using the present integral elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, if present, the element is exposed to any conditioning, such as heating, humidification or the like, that may be desirable to quicken or otherwise facilitate obtaining any test result. If an automated procedure is used, it can also be desirable to have any spreading layer accomplish its function within several seconds, but allowing sufficient time to provide metering.

After the analytical result is obtained as a detectable change, it is measured, usually by passing the element through a zone in which suitable apparatus for reflection, transmission or fluorescence spectrophotometry is provided. Such apparatus would serve to direct a beam of energy, such as light, through the support and the registration layer. The light would then be reflected, such as from a radiation-blocking layer in the element, back to a detecting means or would pass through the element to a detector, in the case of transmission detection. In a preferred mode, the analytical result is detected in a region of the element totally within the region in which such result is produced. Use of reflection spectrophotometry can be advantageous in some situations as it can effectively avoid interference from residues, such as blood cells, which may have been left on or in the layers of the element. Conventional techniques of fluorescence spectrophotometry can also be employed if the detectable ligand is a material which in its free form exhibits an increase or decrease in fluorescence as compared to its fluorescence when bound to the carrier of the bilirubin-active complex. Detection would be accomplished using energy that excites the fluorescent species and a detector that senses its fluorescent emission. Furthermore, when blood serum is tested or means are provided for eliminating unwanted whole blood residues, transmission techniques can be used to detect and quantify the released indicating ligands by directing a flow of radiant energy, for example, U.V. visible or I.R. radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the detectable change produced in the reagent layer can be used. Various calibration techniques can be used to provide a control for the analysis. As one example, a sample of analyte standard solution can be applied adjacent to the area where the drop of sample is placed in order to permit the use of differential measurements in the analysis.

The following Examples are presented as a further illustration of the invention. In these Examples the following materials and abbreviations for these materials are employed:

Bovine or human serum albumin (BSA or HSA, respectively)—both fraction V powders purchased from Pentex, Miles Laboratories, Inc.

8-anilinonaphthalene-1-sulfonate (ANS)—fluorescent probe purchased as the magnesium salt from Eastman Organic Chemicals. This material has the structure

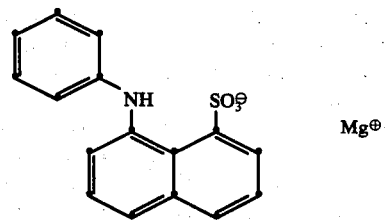

Bilirubin (B)—purchased from Sigma Chemical Company.

Thioflavin S (TF)—fluorescent dye or probe derived from sulfonated methylated benzothiazole. TF was purchased from Matheson, Coleman and Bell, Division of Matheson Co., Inc., Norwood, N.J. This material (sometimes referred to in the literature as vasoflavin) has the following structure

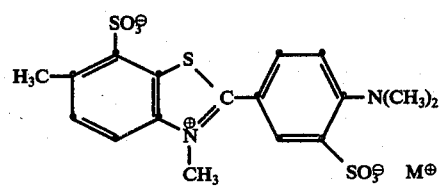

wherein M⊕ is a metallic cation.

Spectrofluorometer—Farrand MD-I spectrofluorometer purchased from Farrand Optical Co., Valhalla, N.Y.

In the following Examples, the amounts of detectable ligand, usually a fluorescent probe or dye, and carrier, usually protein such as HSA or BSA, which form the bilirubin-active complex are referred to as the dye/protein (D/P) ratio. These ratios are molar ratios. Where the detectable ligand used in the following Examples was a fluorescent probe, arbitrary fluorescence, F, was recorded both immediately before and after addition of bilirubin (B) to the complex. The difference in these F values (i.e. $\Delta F$) was then expressed as a percentage value by arbitrarily designating the F value for the complex at 100 prior to addition of any bilirubin analyte to the complex (i.e. at zero B concentration). A series of $\Delta F$ values were then plotted for a given complex having a constant D/P ratio against a series of liquid test samples containing varying B concentrations. As a result, one obtained a calibration curve for that complex. A liquid test sample containing an unknown amount of B, could then be evaluated by the $\Delta F$ value for that sample using the calibrated complex and then locating this $\Delta F$ value on the previously prepared calibration curve for the complex.

EXAMPLE 1

Bilirubin Solution Assay Using Ans-Albumin Complex

In this Example, a solution assay for bilirubin was performed using as the bilirubin-active complex an ANS-albumin complex. In this example, as well as in the succeeding examples, both BSA and HSA gave essentially the same results although, in general, it was noted that HSA produced a more fluorescent complex with ANS than did BSA. In this Example, fluorescence of the ANS-albumin complex was obtained by exciting the complex at an excitation maximum of 386 nanometers. Fluorescent emission from the complex was monitored at both the excitation maximum of 386 nanometers and at the primary fluorescent emission wavelength of 475 nanometers exhibited by the complex. As is known, the fluorescent probe ANS is highly fluorescent when associated with albumin, but is non-fluorescent when free in solution. As shown in this Example in accord with the present invention, ANS binding to albumin is indeed sensitive to bilirubin concentrations in solution. That is, as explained above, ANS was effectively displaced from the bilirubin-active ANS-albumin complex in an amount related to the bilirubin concentration in solution. Thus, by monitoring the changes in $\Delta F$ values as described immediately hereinabove with a spectrofluorometer, one produced an extremely effective solution assay for bilirubin.

Part 1

In this section of Example 1, the effect of varying concentrations of bilirubin on an ANS-albumin complex was established as follows: A series of individual solutions containing varying amounts of ANS were titrated with a series of solutions each containing five micromoles per liter of HSA, and the relative fluorescence, F, was measured using the above-indicated spectrofluorometer. An apparent maximal relative fluorescence was achieved using a level of approximately 15 micromoles per liter of ANS for 5 micromoles per liter of HSA, thereby indicating that approximately 3 moles of ANS bind per one mole of HSA. Thereafter, a sample of each of the above-described bilirubin-active complexes composed of varying ANS/HSA ratios was tested in accordance with the method of the present invention to provide an interactive composition for the assay of bilirubin. In each case, it was found that when, for example, 0.066 milligram per deciliter of bilirubin was added to each of the above-described solutions containing ANS/HSA bilirubin-active complexes, one obtained a drastic reduction in fluorescence, thereby indicating displacement of ANS by bilirubin and release of free ANS into solution. To demonstrate that increasing amounts of bilirubin added to ANS/HSA bilirubin-active complexes produced corresponding greater decreases in arbitrary fluorescence which could be monitored and therefore used to quantitatively determine bilirubin concentration in various biological liquid samples, a solution was prepared containing as the bilirubin-active complex a mixture of 25 micromoles ANS per liter and 15 micromoles per liter HSA. This solution of 25 micromoles per liter ANS and 15 micromoles per liter HSA was then divided into a series of test solutions. The fluorescence of each of these individual test solutions was monitored as bilirubin-containing test samples were admixed into these individual solutions. The bilirubin-containing test samples had varying amounts of bilirubin ranging from a minimum bilirubin concentration of about 0.03 milligrams per deciliter to a maximum of 0.33 milligrams per deciliter. As a result, it was found that indeed a greater drop in arbitrary fluorescence was measured, depending upon the increased amount of bilirubin contained in the liquid. It was found that bilirubin did displace ANS from albumin, and that the extent of displacement monitored by the change in fluorescence was quasi-linearly related to the amount of bilirubin added to the initial ANS/HSA complex.

Part 2

The solution assay for bilirubin using ANS/HSA complexes as described in Part 1 above was then modified by varying the D/P ratio of ANS to HSA or BSA in the solution mixture of ANS and HSA to determine an optimum ratio for bilirubin assay. In addition, the absolute amounts of both the ANS and HSA or BSA added to the solution test mixtures used in the bilirubin assay were varied to optimize this parameter as well. As a result of these further tests, it was found that the solution assay method of the invention when using ANS and HSA or BSA to form the bilirubin-active complex can be practiced over a wide range of varying ANS/HSA or BSA ratios and using widely varying absolute amounts of ANS and HSA or BSA. For example, it was found that the ANS/HSA or BSA ratio could be varied from 1:1 up to 100:1 and achieve useful bilirubin assay measurements. Using an ANS/BSA ratio of 1:1 and an absolute amount of each of ANS and BSA of 5 micromoles per liter, it was found that a solution of this bilirubin-active complex could be used to effectively measure a dynamic range of bilirubin concentration extending from approximately 0 milligrams bilirubin per deciliter to 0.4 milligrams of bilirubin per deciliter. In addition, it was found that by substantially increasing the absolute amount of ANS and BSA used to form the solution of bilirubin-active complex, one could dramatically increase the dynamic range over which a solution of such a complex could be used for bilirubin assay. For example, it was found that a solution of a bilirubin-active complex composed of 1500 micromoles per liter of ANS and 500 micromoles per liter of BSA could be used to quantitatively monitor liquid test samples containing a range of bilirubin concentration extending from about 0 up to about 50 milligrams of bilirubin per deciliter of test sample.

It should be noted that, in Part 1 and Part 2 of this Example, all solutions referred to therein were prepared in 0.05 M sodium phosphate buffer having a pH of 7.4 ± 0.05. It may be further noted that in both Part 1 and Part 2 of this Example it was found that these solution assay tests could be conducted about equally well both at about 37° C and at 20° ± 2° C. Further, in each of Part 1 and Part 2 of this Example, as well as in each of the remaining Examples, all test samples containing bilirubin were prepared, unless otherwise indicated, by adding the indicated amount of crystalline bilirubin to the above-described 0.05 moles sodium phosphate buffer solution using the method of J. Jacobsen and W. Wennberg, as described in *Clinical Chemistry*, Volume 20, page 783 (1974).

EXAMPLE 2

Bilirubin Solution Assay Using Vasoflavin-Albumin Complexes

In this Example, a solution assay for bilirubin was carried out in a manner similar to that described in Example 1 above, except that the bilirubin-active complex was replaced by a vasoflavin-albumin complex. The solutions containing such complexes of vasoflavin and albumin were prepared as described by Betheil, *Analytical Chemistry*, Volume 32, Part 4, page 560, 1960. As a result, in this Example the solutions of vasoflavin-albumin were prepared in an amine buffer at a pH of about 9 as prescribed by Betheil noted above. In addition, in this Example, fluorescence was monitored using an excitation wavelength of 390 nanometers and an emission maximum wavelength of 430 nanometers. The particular amine buffer used in this Example was an ethylene-diamine-citrate buffer and the solution assay measurements in this Example were carried out at a temperature of from about 20° C to 22° C. Under the aforementioned test conditions, it was found that a vasoflavin-albumin solution complex having a vasoflavin/albumin ratio of about 3 to about 1 performed quite well as a bilirubin-active complex in the assay method of the present invention. Again, as in Example 1 above, it was found that one could increase the dynamic range of such a solution assay technique by using larger absolute amounts of vasoflavin and albumin to form the bilirubin-active complex solution. In this regard, it was found that a useful solution assay for bilirubin could be obtained exhibiting a dynamic range for bilirubin varying in amounts from about 0 to about 20 milligrams of bilirubin per deciliter of liquid by use of a bilirubin-active complex solution containing about 0.4 micromoles per liter of vasoflavin and 500 micromoles per liter of HSA.

EXAMPLE 3

Colorimetric Bilirubin Solution Assay Using Bromophenolblue-Albumin Complex

In this Example, a solution assay for bilirubin in accord with the method of the present invention is illustrated. The assay of the present Example is similar to that described in Examples 1 and 2 above, except that the present Example illustrates the use of a colorimetric, rather than a fluorometric, assay using bromophenol blue indicator dye as the detectable ligand in the bilirubin-active complex. In the assay reported in this Example, it was found that bromophenol blue can be bound to various carriers useful in forming bilirubin-active complexes in accord with the present invention and further that bromophenol blue can readily be displaced from such carriers, such as albumin, by bilirubin. It was found that bromophenol blue exhibits a first order binding constant $K_A$ ($M^{-1}$) of $2 \times 10^6$, thus having a useful binding constant in accord with the present invention, i.e., a binding constant to the carrier which is greater than $10^5$ and less than that of bilirubin, bilirubin having a binding constant, for example, to albumin of about $10^8$. Bromophenol blue was further observed to have a relatively high extinction coefficient of approximately 78,000 at a wavelength at or near 590 nanometers. In this Example, a series of solutions of HSA and bromophenol blue were prepared in a 0.05 mole sodium phosphate buffer aqueous solution having a pH of 7.4 as measured at 25° C. Using an Amicon Ultraflo Membrane Cone CF-25 (having a molecular weight cutoff of 25,000 daltons) in an ultrafiltration technique as described by U. Kragh-Hansen et. al., *Biochim. et Biophys. Acta*, Volume 365, page 36 (1974), it was determined that useful bilirubin-active complexes of bromophenol blue and HSA could be prepared in the above-described sodium phosphate buffer aqueous solution using absolute amounts of HSA varying from about 0.20 to about 100 micromoles per liter and amounts of bromophenol blue varying from about 0 to about 12 micromoles per liter, respectively. The molar binding ratio of dye to HSA of the bilirubin-active complex solutions described above was found to vary over a range of from about 0.5 to about 3.4, which was the approximate maximum molar binding ratio of bromophenol blue to HSA. The above series of solutions containing the differing amounts of bromophenol blue/HSA bilirubin-active complexes were then tested by adding to each of these solutions a standard test solution containing about 0.0244 milligrams of bilirubin per deciliter and subjecting the resultant solutions to ultrafiltration, as referred to above, to remove the bromophenol blue displaced by the bilirubin. As a result, a clear-cut decrease, about 33%, in bromophenol blue binding to HSA was observed by spectrometrically monitoring the 590 nanometer absorption maximum for bromophenol blue being released from the solutions as a result of being competitively displaced from the albumin carrier by the bilirubin. Thereafter, a standard test solution having a high bilirubin level of approximately 10 milligrams of bilirubin per deciliter was added to the above-described solutions containing the bromophenol blue/HSA bilirubin-active complexes, and again ultrafiltration was carried out. It was observed that, in this case, a substantially higher amount of bromophenol blue in each of the above-described test solutions was competitively displaced from the albumin carrier by this large amount of bilirubin. The results of this Example demonstrate that one can form a useful colorimetric assay for bilirubin using dyes such as bromophenol blue having an extinction coefficient greater than about 75,000 and the desired binding affinity to a common carrier for both the dye and bilirubin.

EXAMPLE 4

Analytical Element for Bilirubin Assay

In this and in each of the remaining Examples, various configurations of integral, multilayer analytical elements are illustrated which, in accord with the present invention, provide effective elements for a "dry" assay for bilirubin. In this Example, a multilayer element was prepared having a cellulose acetate support, a polyvinyl alcohol (PVA) registration layer coated over the cellulose acetate base at a coverage of about 1.7 g./m.$^2$ PVA to receive released detectable ligand from overcoated layers, a polymeric subbing layer coated over the polyvinyl alcohol registration layer, and a blush polymer spreading-reagent layer containing a bilirubin-active complex composed of a 1:1 molar mixture of the fluorescent probe ANS to HSA, cellulose acetate, Triton X-100® (a nonionic octylphenoxy polyethoxyethenol surfactant sold by Rohm and Haas Co.), and titanium dioxide particles. In this reagent layer, the bilirubin-active complex was coated in an amount of about 5.4 g. of the complex per square meter, the cellulose acetate was coated in an amount of about 6.4 g. per square meter, the Triton X-100® surfactant was coated in an amount of about 1.4 g./m.$^2$, and the titanium dioxide particles were coated in an amount of about 49.5 g./m.$^2$. All coating coverages are based on dry weight of coated material excluding the weight of any liquid coating solvent. The reagent layer was coated from a solvent-nonsolvent solvent mixture consisting of acetone, dichloroethane, and xylene. A series of sample test liquid solutions containing varying amounts of bilirubin ranging from 0 to about 50 milligrams of bilirubin per deciliter and also containing about 7 g/dl of albumin was applied in 10 microliter sample drops to individual spots of the above-described multilayer element. As this was done, a spectrofluorometer was used to measure the fluorescence both immediately before and 5 minutes after each spotted bilirubin sample application. As a result, a calibration curve for bilirubin was generated and the resultant web was found capable of quantitatively evaluating known amounts of bilirubin in various sample solutions subsequently applied to this web which had been calibrated as described above. Each such bilirubin assay using this multilayer element could be performed in about 5 to 7 minutes. The presence of the albumin in the bilirubin sample solutions used to calibrate the analytical element did not appear to interfere with the response of the element to bilirubin. The spectrofluorometer was used to measure fluorescence in this Example in a manner as described in Examples 1 and 2 above, i.e., by using an excitation wavelength of 396 nanometers and monitoring both this excitation wavelength and the emission wavelength maximum of ANS at 475 nanometers. The cellulose acetate base in this Example was selected because it exhibits little or no fluorescence to interfere with the measurements performed in this assay. Therefore, the fluorometric measurements could be made directly through the base of the above-described element. As in Examples 1 and 2 above, the fluorescence measurements clearly demonstrated a quasi-linear decrease in fluorescence exhibited by the bilirubin-active complex located in the reagent layer of the element as the amount of bilirubin in the applied 10 microliter bilirubin-containing test samples were spotted onto the element.

EXAMPLE 5

In this Example, an analytical element in accord with the present invention was prepared having a structure somewhat similar to that described above in Example 4, except that in this Example the bilirubin-active complex was incorporated directly into the polyvinyl alcohol layer described in Example 4 so that this layer no longer functioned as a registration layer, but as the reagent layer for the analytical element of this Example. In addition, the amount of the bilirubin-active complex was modified such that the total amount of albumin incorporated in the polyvinyl alcohol layer was coated in an amount of about 2.7 g./m.$^2$ of element and the amount of ANS was coated in an amount of about 0.027 g./m.$^2$. In the element of this Example, no bilirubin-active complex material was incorporated into the cellulose acetate-titanium dioxide top layer of the element, so that this layer functions solely as a spreading layer in the element of this Example. In this Example, the Triton X-100® surfactant present in the spreading layer was used to normalize the transport of various bilirubin-containing solutions and to enhance the dissociation of any albumin bound to bilirubin in these test samples. In addition, the pore size of the polyvinyl alcohol reagent layer was such that this reagent layer containing polyvinyl alcohol and the bilirubin-active complex was substantially impermeable to albumin. Again, as in Example 4, the element was calibrated using a series of standard test solutions containing varying amounts of bilirubin ranging from 0 to about 50 milligrams bilirubin per deciliter, and then the thus calibrated web was used to determine a series of bilirubin concentrations using unknown bilirubin-containing serum samples. Again, as in Example 4, the bilirubin assay of this element was monitored using a spectrofluorometer. The results of the bilirubin assay conducted using the analytical elements described in Example 4 and in this Example demonstrated that both of these elements exhibited little or no interference due to the presence of albumin in the various bilirubin-containing samples of serum. The dynamic range of both the element in Example 4 and in Example 5 extended up to about 10 milligrams of bilirubin per deciliter. However, within the range of 0 to 10 milligrams bilirubin per deciliter, each of the analytical elements of Examples 4 and 5 produced good quantitative results.

EXAMPLE 6

Figure 4:
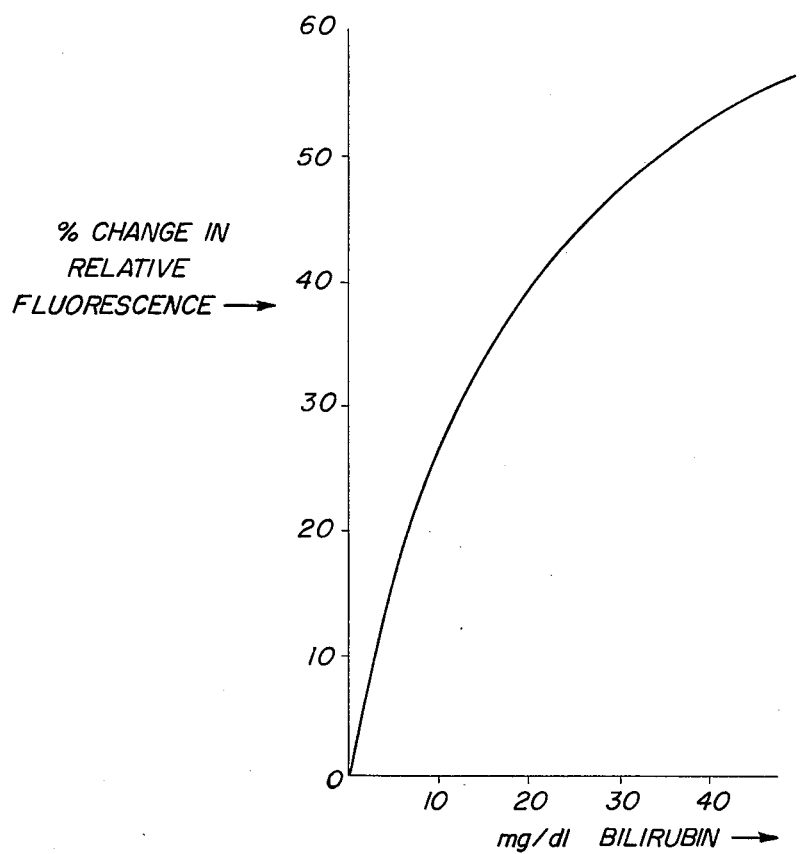
FIG. 4 illustrates a calibration curve obtained for a multilayer analytical element of the invention.

In this Example, a further modification of the structural configuration of the analytical elements described in Examples 4 and 5 was made to obtain a resultant element exhibiting greater dynamic range for bilirubin assay. The element of this Example consisted of a cellulose acetate support; coated over this support was a gelatin registration layer applied from an aqueous solution having a pH of 7.0 and applied at a rate of 5.7 g. of gelatin per square meter of element; coated over the gelatin registration layer was a reagent layer applied from a 0.05 molar sodium phosphate buffer solution having a pH of 7.5 and containing per square meter of coating 2.3 g. pigskin gelatin, 0.27 g. of BSA, and 0.27 g. of the fluorescent probe ANS; and coated over the reagent layer was a blush polymer spreading layer containing 0.34 g/m² of barium sulfate particles, approximately 3.2 grams per square meter of Triton X-100 ® (an octylphenoxy polyethoxyethanol surfactant sold by Rohm & Hass Co.), and approximately 6.4 g/m² of cellulose acetate. The above-described multilayer element was then used as in Examples 4 and 5 above by applying a series of liquid bilirubin spot samples containing varying bilirubin amounts ranging from 0 to 50 milligrams of bilirubin per deciliter to establish a calibration curve for the analytical element described in this Example. FIG. 4 attached hereto illustrates this calibration curve and demonstrates that this multilayer element exhibited discrimination both at very low bilirubin concentrations, i.e., from about 0.1 to about 1 milligram of bilirubin per deciliter and at relatively high bilirubin concentrations, i.e., from 1 to about 20 milligrams per deciliter; again, the element was then tested with a series of test samples containing unknown amounts of bilirubin and was found to produce good quantitative measurements of the bilirubin content of the samples. The element of this Example exhibited little or no interference to the presence of albumin contained in the various bilirubin-containing spot samples and was capable of producing highly reproducible results. Again, the results produced on the element of this Example were obtained using a spectrofluorometer and by monitoring the 386 nanometer excitation maximum of ANS and the emission maximum of ANS bound to albumin at 475 nanometers.

The invention has been described in detail with particular reference to certain preferred embodiments thereof, but it will be understood that variations and modifications can be effected within the spirit and scope of the invention.

We claim:

1. A method for the detection of bilirubin in an aqueous liquid sample which comprises
   a. contacting together in a reagent zone said liquid sample and an interactive composition,
      such interactive composition containing a bilirubin-active complex comprising a diffusible, bilirubin-displaceable, detectable ligand bound to a carrier which can also bind bilirubin, said carrier having a first order binding constant to bilirubin in excess of $10^7$ and a first order binding constant to said detectable ligand which is in excess of $10^5$ but less than the aforementioned binding constant to bilirubin,
   whereby bilirubin displaces said detectable ligand from said interactive composition, and
   b. selectively detecting said detectable ligand.

2. The method of claim 1 wherein said interactive composition is admixed in a non-interfering liquid medium and is contacted together with said liquid sample in said reagent zone at a pH of from about 6.8 to about 9.5 and at a temperature of from about 15° to about 60° C.

3. The method of claim 1 wherein said interactive composition is present in an initially dry reagent zone.

4. The method of claim 1 wherein said interactive composition is present in an initially dry reagent zone which comprises said interactive composition distributed in a polymeric matrix and wherein said liquid sample is contacted together with said interactive composition in said reagent zone at a pH of from about 6.8 to about 9.5 and at a temperature of from about 15° to about 60° C.

5. The method of claim 1 wherein said detectable ligand is a colorimetrically detectable material having a molar extinction coefficient in excess of about 75,000.

6. The method of claim 1 wherein said detectable ligand is fluorimetrically detectable.

7. The method of claim 1 wherein said carrier of said bilirubin-active complex comprises a protein material.

8. The method of claim 1 wherein said carrier of said bilirubin-active complex comprises albumin, an albumin degradation product, or an albumin derivative.

9. The method of claim 1 wherein said liquid sample is a biological fluid.

10. The method of claim 1 wherein said liquid sample is blood serum.

11. The method of claim 1 wherein said liquid sample is blood serum which has been pretreated to reduce the amount of albumin contained therein.

12. The method of claim 1 wherein said detectable ligand is bromophenol blue or chlorophenol red.

13. The method of claim 1 wherein said detectable ligand is a member selected from the group consisting of an 8-anilino-1-naphthalenesulfonate salt, a 6-p-toluidino-2-naphthalene sulfonate salt, a 5-dimethylamino-1-naphthalene sulfonate salt, and a sulfonated methylated benzothiazole derivative.

14. The method of claim 1 wherein said detectable ligand is an 8-anilino-1-naphthalenesulfonate magnesium salt or the sulfonyl chloride derivative of a 6-p-toluidino-2-naphthalene-sulfonate salt.

15. An analytical element for the detection of a bilirubin in an aqueous liquid sample, said element comprising an initially dry reagent zone which comprises an interactive composition for the detection of bilirubin, such interactive composition containing a bilirubin-active complex comprising a diffusible, bilirubin-displaceable, detectable ligand bound to a carrier which can also bind bilirubin, said carrier having a first order binding constant to bilirubin in excess of $10^7$ and a first order binding constant to said detectable ligand which is in excess of $10^5$ but less than the aforementioned binding constant to bilirubin.

16. An analytical element for the detection of a bilirubin in an aqueous liquid sample, said element comprising an initially dry reagent zone and an initially dry spreading zone in fluid contact with one another under conditions of use,
   said reagent zone comprising an interactive composition for the detection of bilirubin, such interactive composition containing a bilirubin-active complex comprising a diffusible, bilirubin-displaceable, detectable ligand bound to a carrier which can also bind bilirubin, said carrier having a first order binding constant to bilirubin in excess of $10^7$ and a first order binding constant to said detectable ligand which is in excess of $10^5$ but less than the aforementioned binding constant to bilirubin, and
   said spreading zone comprising a porous polymeric composition or particulate matter.

17. An analytical element for the detection of a bilirubin in an aqueous liquid sample, said element comprising an initially dry reagent zone and an initially dry registration zone in fluid contact with one another under conditions of use,
   said reagent zone comprising an interactive composition for the detection of bilirubin, such interactive composition containing a bilirubin-active complex comprising a diffusible, bilirubin-displaceable, detectable ligand bound to a carrier which can also bind bilirubin, said carrier having a first order binding constant to bilirubin in excess of $10^7$ and a first order binding constant to said detectable ligand which is in excess of $10^5$ but less than the aforementioned binding constant to bilirubin, and said registration zone comprising material for receiving said diffusible ligand upon displacement thereof by bilirubin.

18. An analytical element for the detection of bilirubin in an aqueous liquid sample, said element comprising a reagent layer superposed on a registration layer carried on a radiation-transmissive support, said reagent layer comprising an interactive composition containing a bilirubin-active complex comprising a diffusible, bilirubin-displaceable, detectable ligand bound to a carrier which can also bind bilirubin, said carrier having a first order binding constant to bilirubin in excess of $10^7$ and a first order binding constant to said detectable ligand which is in excess of $10^5$ but less than the aforementioned binding constant to bilirubin, and said registration layer comprising a material for receiving said diffusible ligand upon displacement thereof by bilirubin.

19. The element of claim 18 wherein said reagent layer is an isotropically porous layer comprising said interactive composition and a porous polymeric composition or particulate matter.

20. The element of claim 18 wherein said element comprises an isotropically porous spreading layer superposed over said reagent layer and in fluid contact therewith under conditions of use, said spreading layer comprising a porous polymeric composition or particulate matter.

21. The element of claim 18 wherein said interactive composition comprises as the detectable ligand a colorimetrically detectable material having a molar extinction coefficient in excess of about 75,000, and wherein said element comprises a radiation-blocking layer interposed between said reagent layer and said registration layer.

22. The element of claim 18 wherein said bilirubin-active complex comprises as the detectable ligand a fluorimetrically detectable material.

23. The element of claim 18 wherein said carrier of said bilirubin-active complex comprises a protein material.

24. The element of claim 18 wherein said carrier of said bilirubin-active complex comprises albumin, an albumin degradation product, or an albumin derivative.

25. The element of claim 18 wherein said bilirubin-active complex comprises as the detectable ligand bromophenol blue or chlorophenol red.

26. The element of claim 18 wherein the bilirubin-active complex comprises as the detectable ligand a member selected from the group consisting of an 8-anilino-1-naphthalene-sulfonate salt, a 6-p-toluidino-2-naphthalene sulfonate salt, a 5-dimethylamino-1-naphthalene sulfonate salt, and a sulfonated methylated benzothiazole derivative.

27. The element of claim 18 wherein the bilirubin-active complex comprises as detectable ligand an 8-anilino-1-naphthalenesulfonate magnesium salt or the sulfonyl chloride derivative of a 6-p-toluidino-2-naphthalene-sulfonate salt.

28. An essentially dry multilayer analytical element for the detection of bilirubin in an aqueous liquid sample, said element comprising an isotropically porous spreading layer superposed over a reagent layer which, in turn, is superposed over a registration layer carried on a radiation-transmissive support, each of said layers in fluid contact with one another under conditions of use, said spreading layer comprising a porous polymeric composition or particulate matter and an amount of surfactant effective to normalize transport of bilirubin therethrough, said reagent layer comprising an interactive composition containing a bilirubin-active complex comprising a diffusible, bilirubin-displaceable, detectable ligand bound to a carrier which can also bind bilirubin, said carrier having a first order binding constant to bilirubin in excess of $10^7$ and a first order binding constant to said detectable ligand which is in excess of $10^5$ but less than the aforementioned binding constant to bilirubin, and said registration layer comprising a material for receiving said diffusible ligand upon displacement thereof by bilirubin.

29. The element of claim 28 wherein said reagent layer is substantially impermeable to materials having a molecular weight equal to or greater than that of albumin.

30. The element of claim 28 wherein said element comprises a radiation-blocking layer interposed between said reagent layer and said registration layer.

31. The element of claim 28 wherein said bilirubin-active complex comprises as the detectable ligand a fluorimetrically detectable material.

32. The element of claim 28 wherein the bilirubin-active complex comprises as the detectable ligand a member selected from the group consisting of an 8-anilino-1-naphthalene-sulfonate salt, a 6-p-toluidino-2-naphthalene sulfonate salt, a 5-dimethylamino-1-naphthalene sulfonate salt, and a sulfonated methylated benzothiazole derivative.

33. The element of claim 28 wherein the bilirubin-active complex comprises as detectable ligand an 8-anilino-1-naphthalenesulfonate magnesium salt or the sulfonyl chloride derivative of a 6-p-toluidino-2-naphthalene-sulfonate salt.

* * * * *

UNITED STATES PATENT AND TRADEMARK OFFICE
CERTIFICATE OF CORRECTION

PATENT NO. : 4,069,016

DATED : January 17, 1978

INVENTOR(S) : Tai-Wing Wu

It is certified that error appears in the above-identified patent and that said Letters Patent are hereby corrected as shown below:

Column 1, last line, "test" should read --text--.

Column 2, line 46, "absorbtivity" should read --absorptivity--.

Column 2, lines 47-48, "absorbtivity" should read --absorptivity--.

Column 2, line 49, "absorbtivity" should read --absorptivity--.

Column 5, line 28, "zone" should read --zones--.

Column 9, approximate line 28, "Polymyzin" should read --Polymyxin--.

Column 9, line 48, "relates" should read --relate--.

Column 10, line 58, "performed" should read --preformed--.

Column 12, lines 35-36, "temperatures which causes" should read --temperature which cause--.

Column 12, line 56, "affecting" should read --effecting--.

Column 13, line 30, "continguous" should read --contiguous--.

Column 14, line 63, "layer" should read --layers--.

Column 19, line 17, "solvent" (second occurrence) should be deleted.

UNITED STATES PATENT AND TRADEMARK OFFICE
CERTIFICATE OF CORRECTION

PATENT NO. : 4,069,016
DATED : January 17, 1978
INVENTOR(S) : Tai-Wing Wu

It is certified that error appears in the above-identified patent and that said Letters Patent are hereby corrected as shown below:

Column 23, line 42, "Ans-Albumin" should read --ANS-Albumin--.

Column 25, line 5, "milligrams" should read --milligram--.

Column 25, line 6, "milligrams" should read --milligram--.

Column 25, line 30, "moles" should read --molar--.

Column 26, line 1, "micromoles" should read --micromole--.

Column 26, line 31, "mole" should read --molar--.

Column 26, line 53, "milligrams" should read --milligram--.

Column 27, line 27, "polyethoxyethenol" should read --polyethoxyethanol--.

Column 29, line 8, "Hass" should read --Haas--.

Signed and Sealed this

Fifth Day of September 1978

[SEAL]

Attest:

RUTH C. MASON
Attesting Officer

DONALD W. BANNER
Commissioner of Patents and Trademarks